United States Patent [19]

Brink et al.

[11] Patent Number: 6,012,153
[45] Date of Patent: Jan. 4, 2000

[54] BATTERY SUPPORT UNIT FOR EXCHANGING INFORMATION WITH A BATTERY MAILBOX

[75] Inventors: Gregory D. Brink; Carl E. Benvegar; Dennis E. Ochs, all of McMinnville; Jonathan N. Andrews, Monmouth, all of Oreg.

[73] Assignee: Hewlett-Parkard Company, Palo Alto, Calif.

[21] Appl. No.: 08/869,663

[22] Filed: Jun. 5, 1997

Related U.S. Application Data

[63] Continuation of application No. 08/442,550, May 16, 1995, abandoned.
[51] Int. Cl.[7] .............................. G06F 15/00; H02J 7/00
[52] U.S. Cl. .............................. 714/47; 714/30; 714/49; 320/3; 320/5; 320/31
[58] Field of Search ......................... 320/3, 5, 31, 21–24; 395/185.02, 183.01, 184.01; 371/22.5, 48, 27; 714/30, 31, 49, 48, 47

[56] References Cited

U.S. PATENT DOCUMENTS

| | | | |
|---|---|---|---|
| 3,268,870 | 8/1966 | Chalker, Jr. et al. | 395/185.01 |
| 3,579,196 | 5/1971 | Gregg et al. | 395/185.01 |
| 4,080,558 | 3/1978 | Sullivan | 320/39 |
| 4,100,605 | 7/1978 | Holman | 364/900 |
| 4,167,041 | 9/1979 | Curlander et al. | 364/900 |
| 4,289,836 | 9/1981 | Lemelson | 429/61 |
| 4,302,714 | 11/1981 | Yefsky | 320/5 |
| 4,433,387 | 2/1984 | Dyes et al. | 364/900 |
| 4,455,523 | 6/1984 | Koneck et al. | 320/43 |
| 4,553,081 | 11/1985 | Koenck | 320/43 |
| 4,707,795 | 11/1987 | Alber | 364/550 |
| 4,709,202 | 11/1987 | Koenck et al. | 320/43 |
| 4,743,831 | 5/1988 | Young | 320/48 |
| 4,800,336 | 1/1989 | Mikami et al. | 324/426 |
| 4,876,495 | 10/1989 | Palanisamy et al. | 320/18 |
| 4,885,523 | 12/1989 | Koenck | 320/21 |
| 5,130,659 | 7/1992 | Sloan | 324/435 |
| 5,160,880 | 11/1992 | Palanisamy | 320/32 |
| 5,252,906 | 10/1993 | Busson | 320/22 |
| 5,254,931 | 10/1993 | Martensson | 320/22 |
| 5,278,487 | 1/1994 | Koenck | 320/21 |
| 5,371,543 | 12/1994 | Fernandez | 320/5 |
| 5,406,266 | 4/1995 | Mino et al. | 340/636 |
| 5,455,499 | 10/1995 | Uskali et al. | 320/43 |
| 5,487,002 | 1/1996 | Diller et al. | 364/424.01 |
| 5,493,272 | 2/1996 | Beghelli | 340/505 |
| 5,508,599 | 4/1996 | Koenck | 320/21 |
| 5,546,317 | 8/1996 | Andrieu | 364/481 |

FOREIGN PATENT DOCUMENTS

| | | | |
|---|---|---|---|
| 523526 A2 | 7/1992 | European Pat. Off. | H01M 10/48 |
| 622863A1 | 10/1993 | European Pat. Off. | H01M 10/44 |
| WO 92/22099 | 12/1992 | WIPO | H01M 10/48 |

OTHER PUBLICATIONS

J. M. Rosenberg, *Dictionary of Computers, Information Processing, and Telecommunications*, 2nd ed., pp. 363, 1984.

Notebook Battery Management . . . Optimized Battery Information to Uses, Edge: Workgroup Computing Report, Apr. 22, 1996.

Battery Chargers' Integrated firmware, Software packages, Battery & EV Technology, vol. 21, No. 1, May 1, 96.

Chu, D.W., Tradeoffs in implementing intelligent battery management, IEEE, 1996.

Benchmarq Microelectronics, Inc. 1995 Data Book, bq2010 Gas Gauge IC, pp. 2–209 to 2–227.

Intel System Management Bus Specification, Revision 1.0, Feb. 15, 1995, pp. iii–17.

*Primary Examiner*—Norman M. Wright
*Attorney, Agent, or Firm*—Curtis G. Rose

[57] ABSTRACT

A battery support unit, such as a defibrillator battery charger, tests a battery having a memory for an error condition. If the battery support unit finds an error condition with the battery, it transmits error data to a mailbox located in the battery's memory. Other battery support units or electronic devices, or even this battery support unit at a later date, can read the error data in the mailbox and take an appropriate action. For example, the battery support unit can read the mailbox and, if it finds error data placed there by itself, another battery support unit, or an electronic device, enable an indicator, such as an indicator that informs a user that maintenance needs to be performed on the battery. When battery maintenance has been selected, the battery support unit reconditions the battery by charging and discharging the battery a predetermined number of times, and also performs additional testing on the battery.

30 Claims, 14 Drawing Sheets

Prior Art

| SYMBOL | REGISTER NAME | LOC. (HEX) | READ/ WRITE | 7(MSB) |
|---|---|---|---|---|
| CMDR | COMMAND REGISTER | 00h | WRITE | W/$\overline{R}$ |
| FLGS1 | PRIMARY STATUS FLAGS REGISTER | 01h | READ | CHGS |
| TMPGG | TEMPERATURE AND GAS GAUGE REGISTER | 02h | READ | TMPS |
| NACH | NOMINAL AVAILABLE CHARGE HIGH BYTE REGISTER | 03h | R/W | NACH7 |
| NACL | NOMINAL AVAILABLE CHARGE LOW BYTE REGISTER | 17h | READ | NACL7 |
| BATID | BATTERY IDENTIFICATION REGISTER | 04h | R/W | BATID7 |
| LMD | LAST MEASURED DISCHARGE REGISTER | 05h | R/W | LMD7 |
| FLGS2 | SECONDARY STATUS FLAGS REGISTER | 06h | READ | CR |
| PPD | PROGRAM PIN PULL-DOWN REGISTER | 07h | READ | N/U |
| PPU | PROGRAM PIN PULL-UP REGISTER | 08h | READ | N/U |
| CPI | CAPACITY INACCURATE COUNT REGISTER | 09h | READ | CPI7 |
| DMF | DIGITAL MAGNITUDE FILTER REGISTER | 0ah | R/W | DMF7 |
| RST | RESET REGISTER | 39h | WRITE | RST |

NOTE: N/U=NOT USED

FIG.2B

Prior Art

| CONTROL FIELD | | | | | | |
|---|---|---|---|---|---|---|
| 6 | 5 | 4 | 3 | 2 | 1 | 0(LSB) |
| AD6 | AD5 | AD4 | AD3 | AD2 | AD1 | AD0 |
| BRP | BRM | CI | VDQ | N/U | EDV1 | EDVF |
| TMP2 | TMP1 | TMP0 | GGS | GG2 | GG1 | GG0 |
| NACH6 | NACH5 | NACH4 | NACH3 | NACH2 | NACH1 | NACH0 |
| NACL6 | NACL5 | NACL4 | NACL3 | NACL2 | NACL1 | NACL0 |
| BATID6 | BATID5 | BATID4 | BATID3 | BATID2 | BATID1 | BATID0 |
| LMD6 | LMD5 | LMD4 | LMD3 | LMD2 | LMD1 | LMD0 |
| DR2 | DR1 | DR0 | N/U | N/U | N/U | OVLD |
| N/U | PPD6 | PPD5 | PPD4 | PPD3 | PPD2 | PPD1 |
| N/U | PPU6 | PPU5 | PPU4 | PPU3 | PPU2 | PPU1 |
| CPI6 | CPI5 | CPI4 | CPI3 | CPI2 | CPI1 | CPI0 |
| DMF6 | DMF5 | DMF4 | DMF3 | DMF2 | DMF1 | DMF0 |
| 0 | 0 | 0 | 0 | 0 | 0 | 0 |

FIG.2C

| BIT | CODE | DESCRIPTION |
|---|---|---|
| 0 | DRF | DEVICE RECOGNIZED ERROR |
| 1 | CRF | TESTER RECOGNIZED ERROR |
| 2 | BCI | BATTERY CAPACITY INACCURATE |
| 3 | TIP | TEST IN PROGRESS |
| 4 | LTF | LAST CAPACITY TEST FAILED |
| 5 | CTF | ANY CAPACITY TEST FAILED |
| 6 | ERR0 | CHECKSUM—LEAST SIGNIFICANT BIT |
| 7 | ERR1 | CHECKSUM—MOST SIGNIFICANT BIT |

BATTERY SUPPORT UNIT FOR EXCHANGING INFORMATION WITH A BATTERY MAILBOX

CROSS REFERENCE TO RELATED APPLICATION

This is a continuation of application Ser. No. 08/442,550 filed on May 16, 1995, now abandoned.

FIELD OF THE INVENTION

This invention relates to the electronics circuitry field. More particularly, this invention is a battery support unit for exchanging information with a battery mailbox.

BACKGROUND OF THE INVENTION

It has been known for decades that electronic devices can be powered by batteries. Early electronic devices, such as transistor radios, were among the first such devices to be powered by batteries. Later electronic devices to be battery powered include dictation machines, CD players, portable computers, and even transportable medical equipment such as ambulatory heart monitors and defibrillators.

While the lack of intelligence of early electronic devices were a good match for the lack of intelligence of early batteries, the situation today is not so evenly matched. Electronic devices have gotten dramatically more intelligent, advanced and complicated over the years, while batteries have until recently stayed pretty much the same— dumb hunks of encased chemicals that provide power to just about anything hooked up between its contacts until the energy stored in the battery is depleted. An advancement was made when dumb batteries came in two styles— disposable and rechargeable—but being rechargeable didn't make the batteries any smarter.

While a dumb electronic device such as a transistor radio doesn't much care if it is powered by a dumb battery, smarter electronic devices such as computers and medical devices have a higher degree of dependence on a battery that can provide a known amount of power for a known amount of time in a reliable manner. When such smart electronic devices are hooked up to dumb batteries that can die without notice or warning, the operation of the electronic device itself can be undesirably uninterrupted. This interruption can range from annoying—as in the case of a portable computer whose battery unexpectedly dies while its user is composing the world's greatest novel, to deadly—as in the case of a transportable defibrillator whose battery dies during an attempt to resuscitate a patient whose heart is in ventricular fibrillation.

In the last couple of years, so-called "smart" batteries have arrived on the scene to partially address the above problem. These smart batteries, such as those described in the Intel/Duracell Smart Battery Specifications Manual, is defined as a battery pack that contains one or more of the following properties: chemistry self-identification, charge control, fuel gauging, or a communication port. These properties allow a smart electronic device to query the battery and find out what kind of battery it is and how much "fuel", or charge, it has left.

While smart batteries provide information that is helpful in avoiding some of the ways the operation of an electronic device can be interrupted due to unexpected battery failure, they only address a portion of the ways the operation of an electronic device can be interrupted due to unexpected battery failure. Specifically, smart batteries that are working as designed and intended can tell an electronic device in a fairly reliable manner how much power it has left. But smart batteries that are not operating in an expected manner, such as batteries that have been abused, are leaking, are out of calibration, or have an internal error such as a short or open circuit, cannot be trusted to give accurate information about themselves. In these cases, the battery may believe it has several minutes or hours of charge left when in fact it is dead or nearly dead. While this shortcoming of these smart batteries may be tolerable in electronic devices where unexpected battery failure is a simple annoyance, it cannot be tolerated in electronic devices where unexpected battery failure can result in the failure of a defibrillator to revive a patient whose heart is in ventricular fibrillation.

SUMMARY OF THE INVENTION

A battery support unit, such as a defibrillator battery charger, tests a battery having a memory for an error condition. If the battery support unit finds an error condition with the battery, it transmits error data to a mailbox located in the battery's memory. Other battery support units or electronic devices, or even this battery support unit at a later date, can read the error data in the mailbox and take an appropriate action. For example, the battery support unit can read the mailbox and, if it finds error data placed there by itself, another battery support unit, or an electronic device, enable an indicator, such as an indicator that informs a user that maintenance needs to be performed on the battery. When battery maintenance has been selected, the battery support unit reconditions the battery by charging and discharging the battery a predetermined number of times, and also performs additional testing on the battery.

DESCRIPTION OF THE DRAWINGS

FIGS. 2A–2C show the organization of the battery memory in the preferred embodiment of the invention.

FIG. 3 shows the mailbox contained in the battery memory in the preferred embodiment of the invention in more detail.

DETAILED DESCRIPTION OF THE PREFERRED EMBODIMENT

Figure 1:
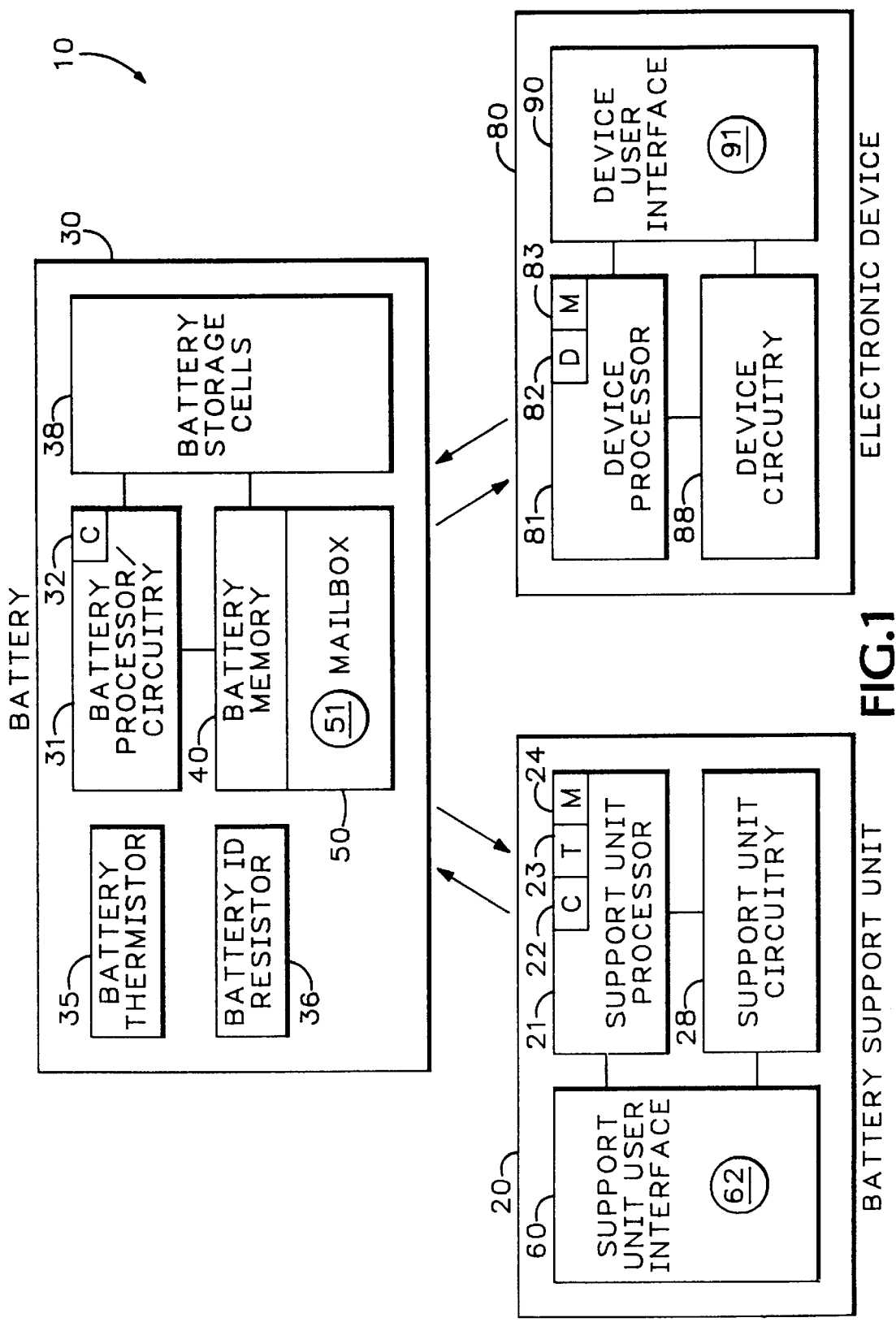
FIG. 1 shows a block diagram of the battery support unit, battery, and electronic device of the system of the preferred embodiment of the invention.

FIG. 1 shows a block diagram of the battery support unit, battery, and electronic device of system 10 of the preferred embodiment of the invention. Battery support unit 20 contains support unit processor 21 connected to support unit circuitry 28 and support unit user interface 60. Support unit user interface 60 will be discussed in more detail later in conjunction with the discussion of FIG. 4. Processor 21 is suitably programmed to execute the flowcharts of FIGS. 6–7 and 8–10 of this invention. Processor 21 contains charger logic unit 22, test logic unit 23, and maintenance logic unit 24. In the preferred embodiment, the functions of logic units 22–24 are performed by software executing the flowcharts of FIGS. 6–7 and 8–10 of the invention, although specific hardware could be fabricated to perform the function of one or more of these logic units, either within processor 21 or in one or more other hardware integrated circuits or other devices, and still fall within the spirit and scope of the invention. In the preferred embodiment, battery support unit 20 charges, tests, and maintains defibrillator batteries, although other battery support units could be used to perform these or different functions and still fall within the spirit and scope of the invention.

Battery 30 contains battery processor/circuitry 31 connected to battery storage cells 38 and battery memory 40. Contained in battery memory 40 is mailbox 50. Both battery memory 40 and mailbox 50 will be discussed later in conjunction with the discussion of FIGS. 2 and 3. Processor/circuitry 31 is suitably programmed to execute the flowchart of FIG. 12 of this invention. Processor/circuitry 31 contains communications logic unit 32. In the preferred embodiment, the functions of logic unit 32 are performed by software executing the flowchart of FIG. 12 of the invention, although specific hardware could be fabricated to perform the function of this logic unit, either within processor/circuitry 21 or in one or more other hardware integrated circuits or other devices, and still fall within the spirit and scope of the invention. Thermistor 35 and battery ID resistor 36 are also contained in battery 30. Thermistor 35 is used to measure the temperature of battery 30, in a manner that will be discussed later. Battery ID resistor 36 is used to uniquely identify the type of battery 30, based on a measured voltage across this resistor. In the preferred embodiment, battery 30 communicates with battery support unit 20 and/or electronic device 80 via six data lines, as follows:

1. Ground
2. V+
3. V+
4. Communications line
5. ID resistor
6. Thermistor

In the preferred embodiment, battery storage cells 38 is a Sanyo NiCAD rechargeable battery, and components 31, 32, and 40 are contained on a Benchmarq bq2010 chip, although battery 30 could be a different type made by a different manufacturer or according to a different standard and still fall within the spirit and scope of the invention. An alternate embodiment has been contemplated where battery 30 just contains storage cells 38 and battery memory 40, where data can be read out of and written to memory 40. In this embodiment, battery memory 40 could be an Econoram RAM with serial port protocol communications, or an EEPROM formatted in accordance with the invention.

Electronic device 80 contains device processor 81 connected to device circuitry 88 and device user interface 90. Device user interface 90 will be discussed in more detail later in conjunction with the discussion of FIG. 5. Processor 81 is suitably programmed to execute the flowchart of FIG. 11 of this invention. Processor 81 contains device logic unit 82, and battery monitor logic unit 83. In the preferred embodiment, the function of logic unit 83 is performed by software executing the flowchart of FIG. 11 of the invention, although specific hardware could be fabricated to perform the function of this logic unit, either within processor 81 or in one or more other hardware integrated circuits or other devices, and still fall within the spirit and scope of the invention. In the preferred embodiment, electronic device 80 is a defibrillator/heart monitor, although other devices, such as a defibrillator or a portable computer, could be used and still fall within the spirit and scope of the invention.

As will be described in more detail later, the bi-directional arrows shown in FIG. 1 symbolize the operation of the preferred embodiment of the invention. When battery 30 is placed in or otherwise connected to battery support unit 20, battery support unit 20 tests battery 30 for an error condition. If battery support unit 20 finds an error condition with battery 30, it transmits error data 51 to mailbox 50 located in battery memory 40. When battery 20 is then removed or otherwise disconnected from battery support unit 20 and placed in or otherwise connected to electronic device 80, electronic device 80 can read error data 51 in mailbox 50 and take an appropriate action. For example, electronic device 80 reads mailbox 50 and finds error data 51 placed there by battery support unit 20. In response to finding error data 51, electronic device 80 enables an indicator, such as indicator 91 in device user interface 90, that informs a user that maintenance needs to be performed on battery 20. The user can continue using battery 20, knowing that its operation is likely to be unreliable, or can remove it from electronic device 80 and insert it into battery support unit 20 for maintenance. When battery maintenance has been selected, battery support unit 20 reconditions battery 30 by charging and discharging the battery a predetermined number of times, and also performs additional testing on battery 30.

Figure 2A:
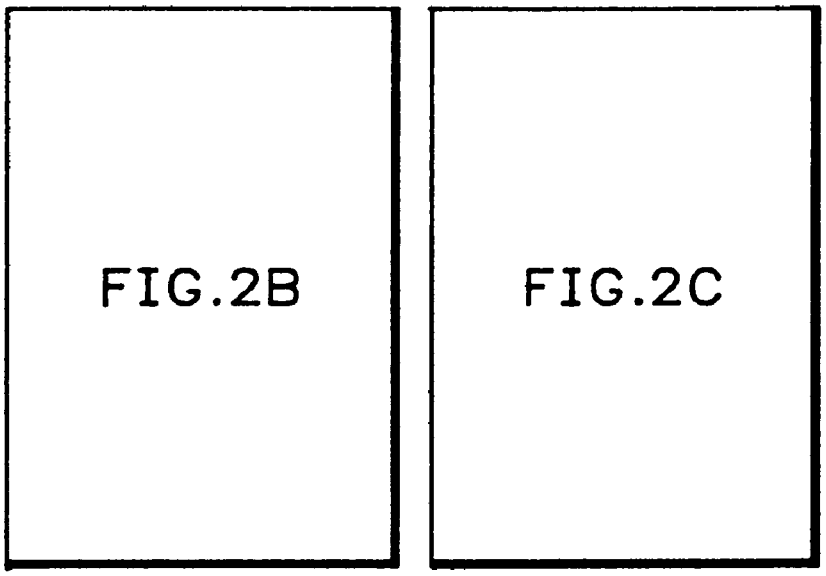

FIGS. 2A–2C show battery memory 40 in more detail. Memory 40 contains a number of registers 41-1 to 41-12. These registers contain status information about battery 40, such as temperature, available charge, and number of times charged. In the preferred embodiment, memory 40 is organized according to the Benchmarq 2010 data sheet, generally available to the public as of the date of this invention.

Memory 40 also contains register 50. Register 50 is identified in FIGS. 2A–2C as "BATID", or "Battery Identification Register". In the Benchmarq 2010 data sheet, this field is described as follows:

The read/write BATID register (address=04h) is available for use by the system to determine the type of battery pack. The BATID contents are retained as long as Vcc is greater than 2V. The contents of BATID have no effect on the bq2010. There is no default setting for this register.

In the preferred embodiment of this invention, battery ID resistor 36 is used to perform the function of BATID register, as discussed above. Therefore, the BATID register is not used as described above, but is instead used as mailbox 50 to exchange information such as error information. The organization of mailbox 50 is shown in FIG. 3. Bit 0 contains a location for a device recognized fault error. If electronic device 80 detects an error with battery 30 in a manner that will be described in more detail later, it puts a "1" in the bit 0 position of mailbox 50. Bit 1 contains a location for a support unit recognized fault error. If battery support unit 20 detects an error with battery 30 in a manner that will be described in more detail later, it puts a "1" in the bit 1 position of mailbox 50. Bit 2 contains a location for a battery capacity inaccurate error. If battery support unit 20 detects that the battery capacity of battery 30 is inaccurate in a manner that will be described in more detail later, it puts a "1" in the bit 2 position of mailbox 50. Bit 3 contains a location for a test in progress flag. This flag is not relevant to the invention and will not be discussed further.

Bit 4 contains a location for a last capacity test failed error. If battery support unit 20 detects that the battery 30 failed its capacity test in a manner that will be described in more detail later, it puts a "1" in the bit 4 position of mailbox 50. Bit 5 contains a location for an any capacity test failed error. If battery support unit 20 detects that battery 30 failed any capacity test in a manner that will be described in more detail later, it puts a "1" in the bit 5 position of mailbox 50.

Bits 6 and 7 of mailbox 50 are used to validate that the other bits are correct by providing a two's complement checksum of the other bits in a manner well known to those skilled in the art.

Figure 4:
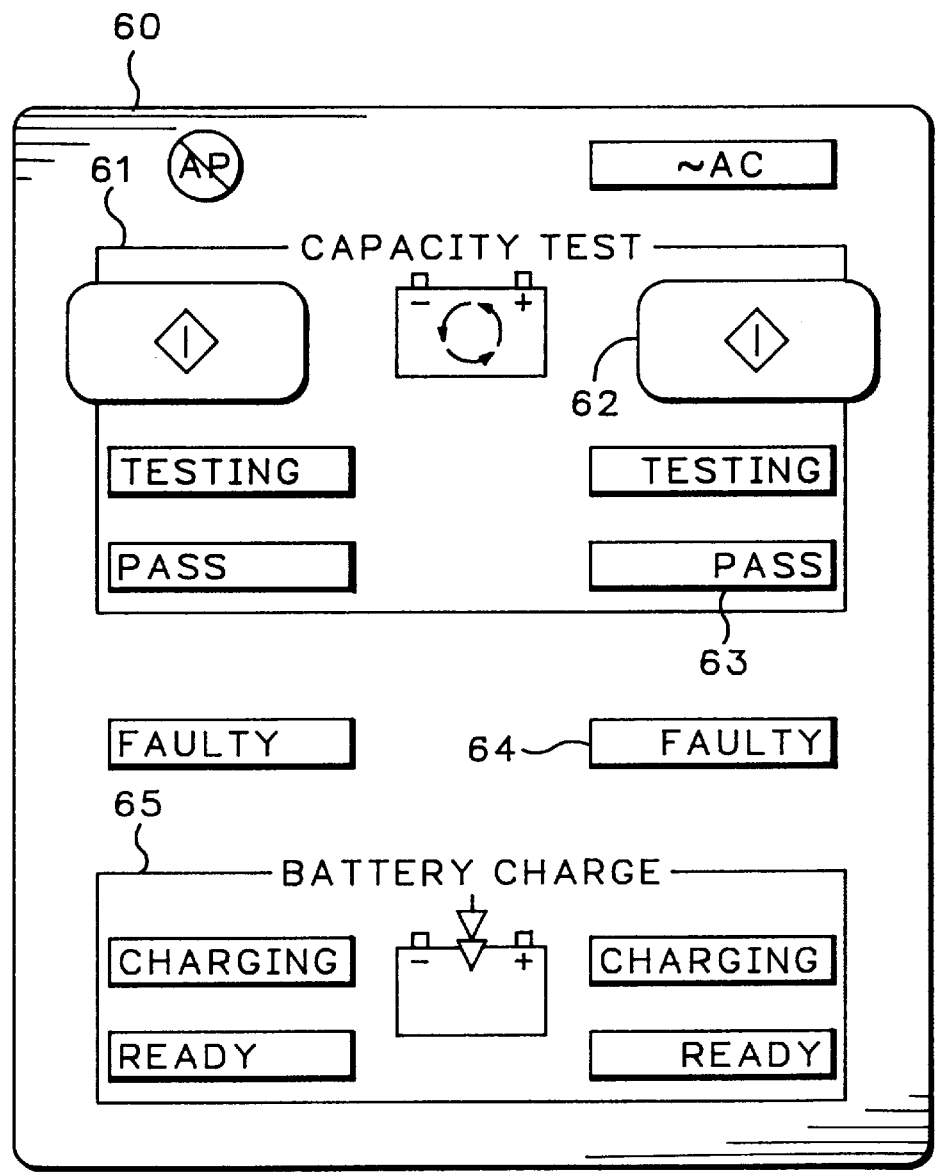
FIG. 4 shows the user interface contained in the battery support unit of the preferred embodiment of the invention.

FIG. 4 shows user interface 60 of battery support unit 20 of the preferred embodiment of the invention. User interface 60 contains maintenance portion 61 and charge portion 65. Maintenance portion 61 contains indicator 62. In the preferred embodiment, indicator 62 is illuminated or otherwise enabled when battery support unit 20 determines that battery maintenance is required, in a manner that will be described in more detail later. When indicator 62 is pressed by a user, battery maintenance is performed.

Figure 5:
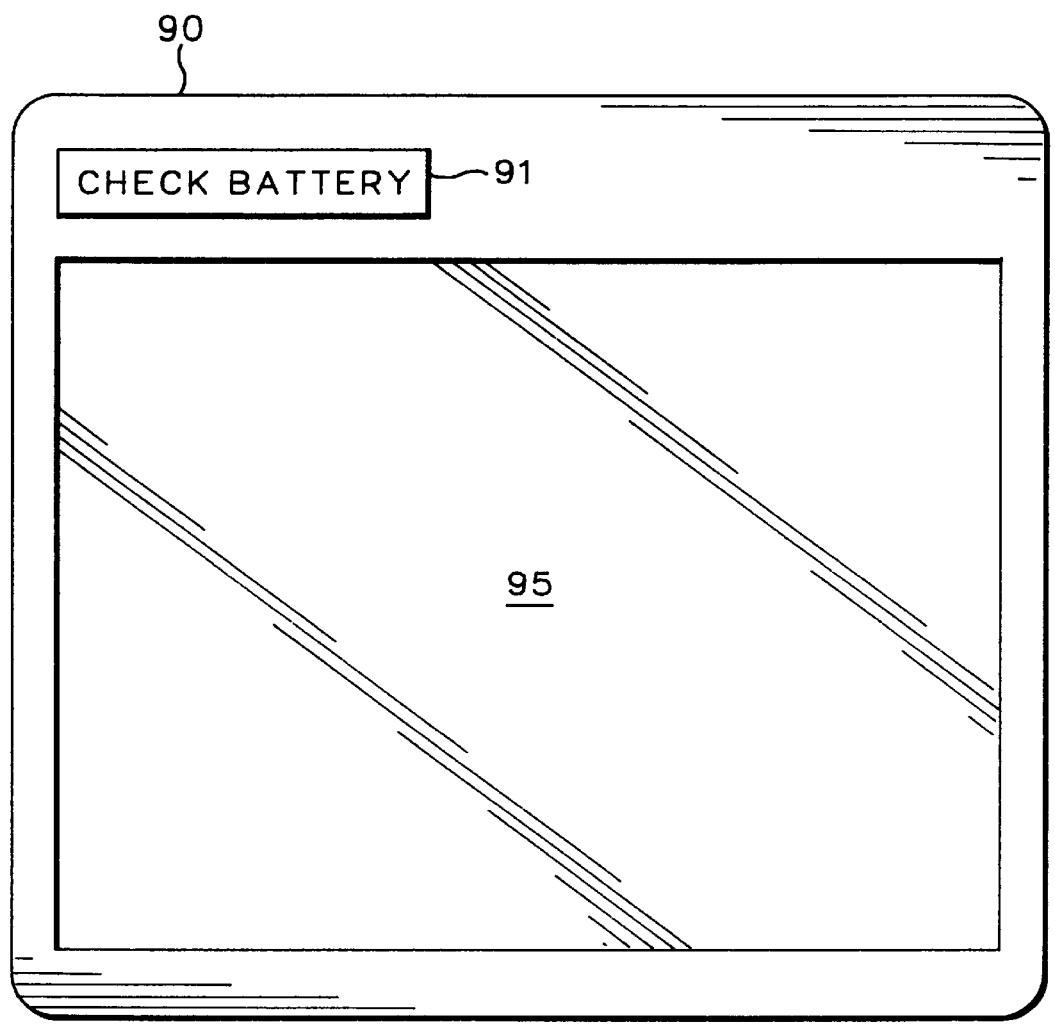
FIG. 5 shows the user interface contained in the electronic device of the preferred embodiment of the invention.

FIG. 5 shows user interface 90 of electronic device 80 of the preferred embodiment of the invention. In the preferred embodiment, user interface 90 is a display screen that contains indicator 91 and device specific display information 95. Indicator 91, when it appears on the display screen of user interface 90, instructs a user to perform maintenance on battery 30. Other types of indicators, such as icons or switches, lights, etc, on a control panel, could be used for indicator 91 and still fall within the spirit and scope of the invention.

Figure 6:
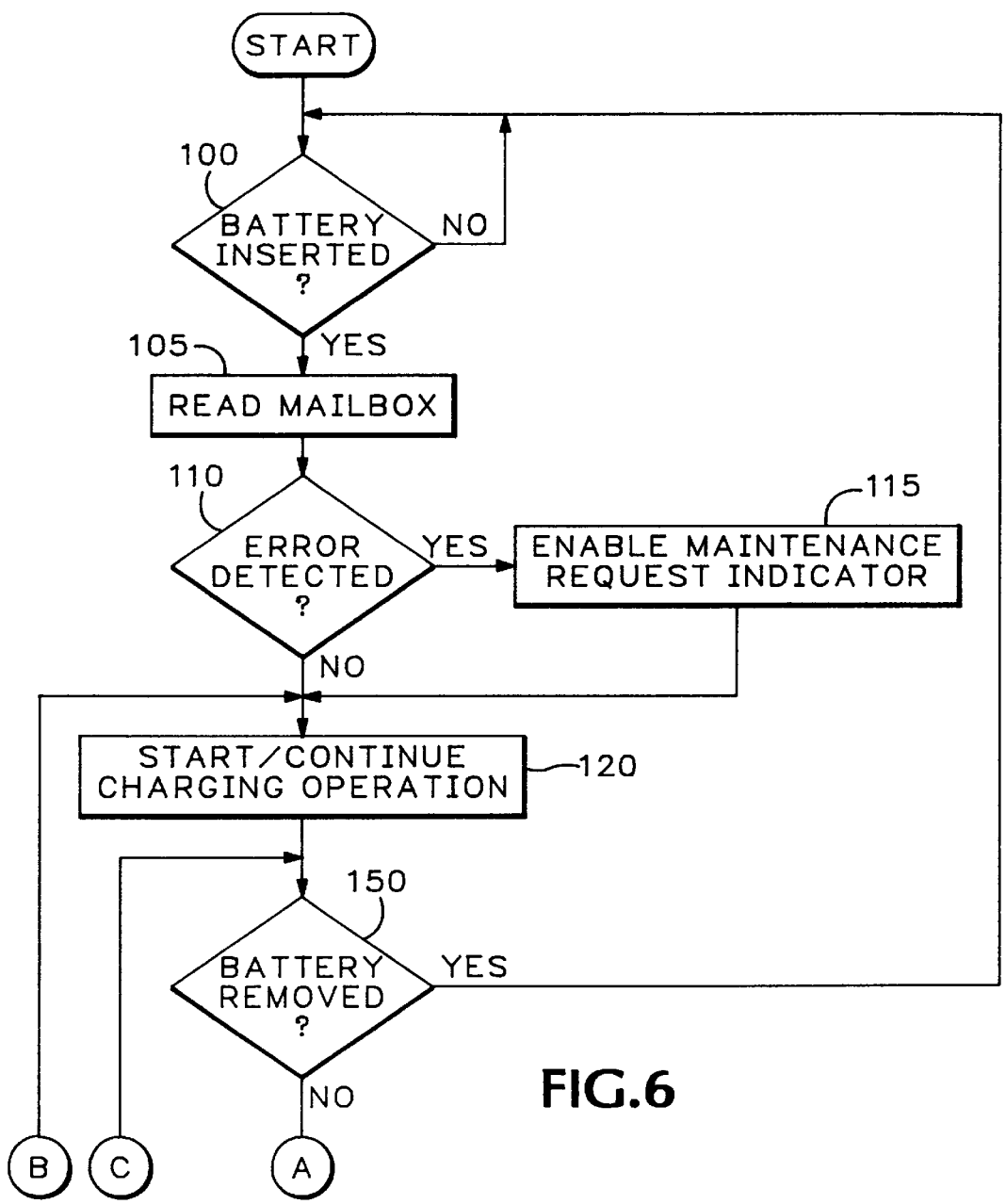
FIGS. 6–7 show the flowchart of the charging operation of the battery support unit of the preferred embodiment of the invention.
Figure 7:
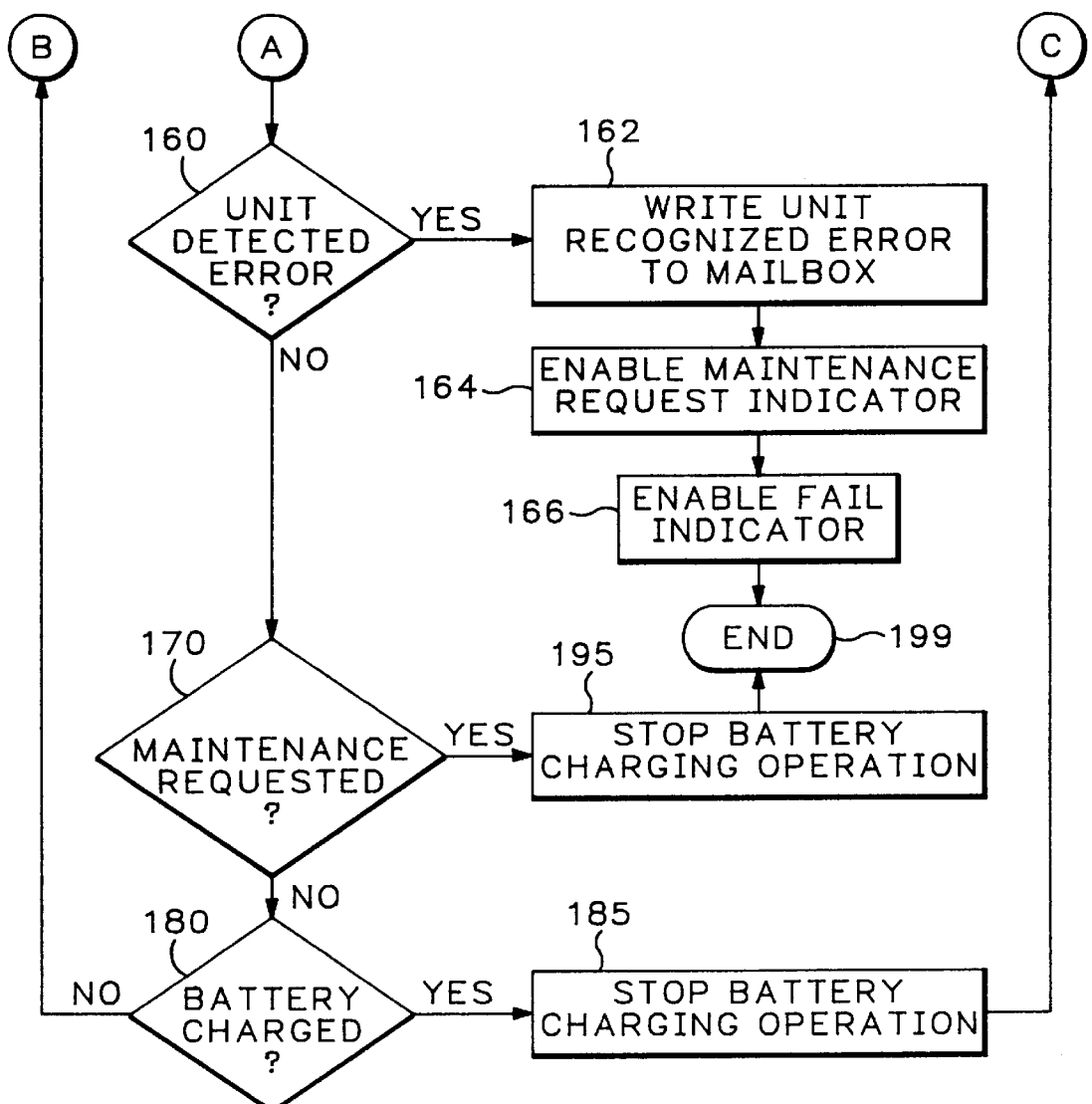

FIGS. 6–7 show the flowchart of the charging operation of battery support unit 20. Block 100 checks to see if a battery is inserted into the charger. When a battery is detected, block 105 reads the contents of mailbox 50 by sending a command to battery 30 to transmit the contents of the register address containing mailbox 50.

Block 110 checks to see if the data contained in mailbox 50 indicates that an error has occurred. For purposes of this discussion, an "error" is defined as the occurrence of an event that indicates that a fault has been detected with the battery that may impact its future performance. A normally functioning rechargeable battery that happens to be discharged and needs to be recharged is not, by itself, considered an "error" for purposes of this invention. When an error is detected, maintenance should normally be performed on battery 50. Errors can be detected and indicated in mailbox 50 by one or more battery support units and/or one or more electronic devices. This is desirable in some operating environments that do not have a one-to-one correspondence of battery support units and electronic devices. One such environment could be a fire station, that might have, for example, four battery support units, ten electronic devices, and thirty batteries—all interchangeable with each other. In this environment, it is desirable for any specific battery support unit to know if another battery support unit detected an error with a particular battery. Likewise, it is desirable for any specific electronic device to know if another electronic device detected an error with a particular battery.

Block 110 checks to see if bits 0, 1, 2, or 4 or mailbox 50 is a "1". Note that a "1" in bit position 5, "Any Capacity Test Failed", is informational in nature and not considered an error of any by itself. If block 110 determines that any of the above bits is a "1", block 115 enables indicator 62 in support unit user interface 60. In the preferred embodiment, this action illuminates a switch that, when pressed by the user, initiates battery maintenance. In the preferred embodiment, maintenance is not initiated automatically but is initiated by a user. This is done because the battery maintenance (described in more detail in FIGS. 8–10) is a lengthy process, often encompassing several hours, and it may not be a convenient time to perform battery maintenance when indicator 62 is first illuminated. However, illumination of indicator 62 puts the user on notice that operation of the battery may not be reliable, and that maintenance should be performed soon. Conversely, when indicator 62 is not illuminated, this tells the user that maintenance is not required, thereby discouraging the user from performing an unnecessary, time consuming process that, if performed more often than needed, could actually shorten battery life.

An alternate embodiment has been contemplated where maintenance is automatically performed upon the detection of an error in block 110. In this embodiment, block 115 is replaced by a block 115' that automatically selects maintenance. The flowchart of FIG. 6 ends in this embodiment after block 115' is executed.

Block 120 starts the charging operation. In the preferred embodiment, charging of battery 30 is automatically initiated when battery 30 is inserted in or otherwise connected to battery support unit 20. The charging operation shown in block 120 starts with a slow, trickle charge for a short period of time, followed by a normal "fast" charge until the battery is fully charged. During the charging operation, blocks 150–199 execute, looking for various conditions that can occur during the charging operation. Block 150 checks to see if the battery was removed before charging was complete. If so, flow of control returns back to block 100 to check for re-insertion of the battery. If not, block 160 (FIG. 7) checks for a support unit detected error that occurred during the charge operation. Examples of errors that can be detected by block 160 are the following: battery too hot, battery too cold, battery voltage too low, battery voltage too high, battery charging timeout (taking too long to charge). Battery support unit 20 determines if a temperature error has occurred by measuring the voltage across thermistor 35 and converting this voltage to temperature in a known manner. Battery support unit 20 determines if a voltage error has occurred by using a portion of support unit circuitry 28 to measure the voltage across battery 30. Battery support unit 20 determines if a timeout error has occurred by using a timer in processor 21 or support unit circuitry 28 to keep track of the elapsed charging time.

If block 160 detects an error, block 162 writes a support unit recognized error to mailbox 50. This is done by placing a "1" in bit 1 of the word read from mailbox 50, adjusting checksum bits 6 and 7 accordingly, and sending the word back to battery 30 as a request to write data to mailbox 50. Block 164 turns on maintenance request indicator 62. Block 166 enables fail indicator 64 (FIG. 4), and the program ends in block 199.

If block 160 does not detect an error, block 170 checks to see if maintenance has been requested. In the preferred embodiment, maintenance is requested by a user pressing indicator 62, as has been discussed. If block 170 is answered affirmatively, the battery charging operation is stopped in block 175, and the program ends in block 199. If block 170 is answered negatively, block 180 checks to see if the battery is fully charged. This is determined by examining the voltage waveform over time and detecting the peak of the voltage curve by looking for $-\Delta v$ (the point on the curve the voltage goes down) in a known manner.

If block 180 determines that the battery is not fully charged, flow of control returns to block 120, where the charging operation is continued. If block 180 determines that the battery is fully charged, block 185 stops the charging operation, and flow of control returns to block 150, where the battery is continuously checked for errors until removed from battery support unit 20.

Figure 8:
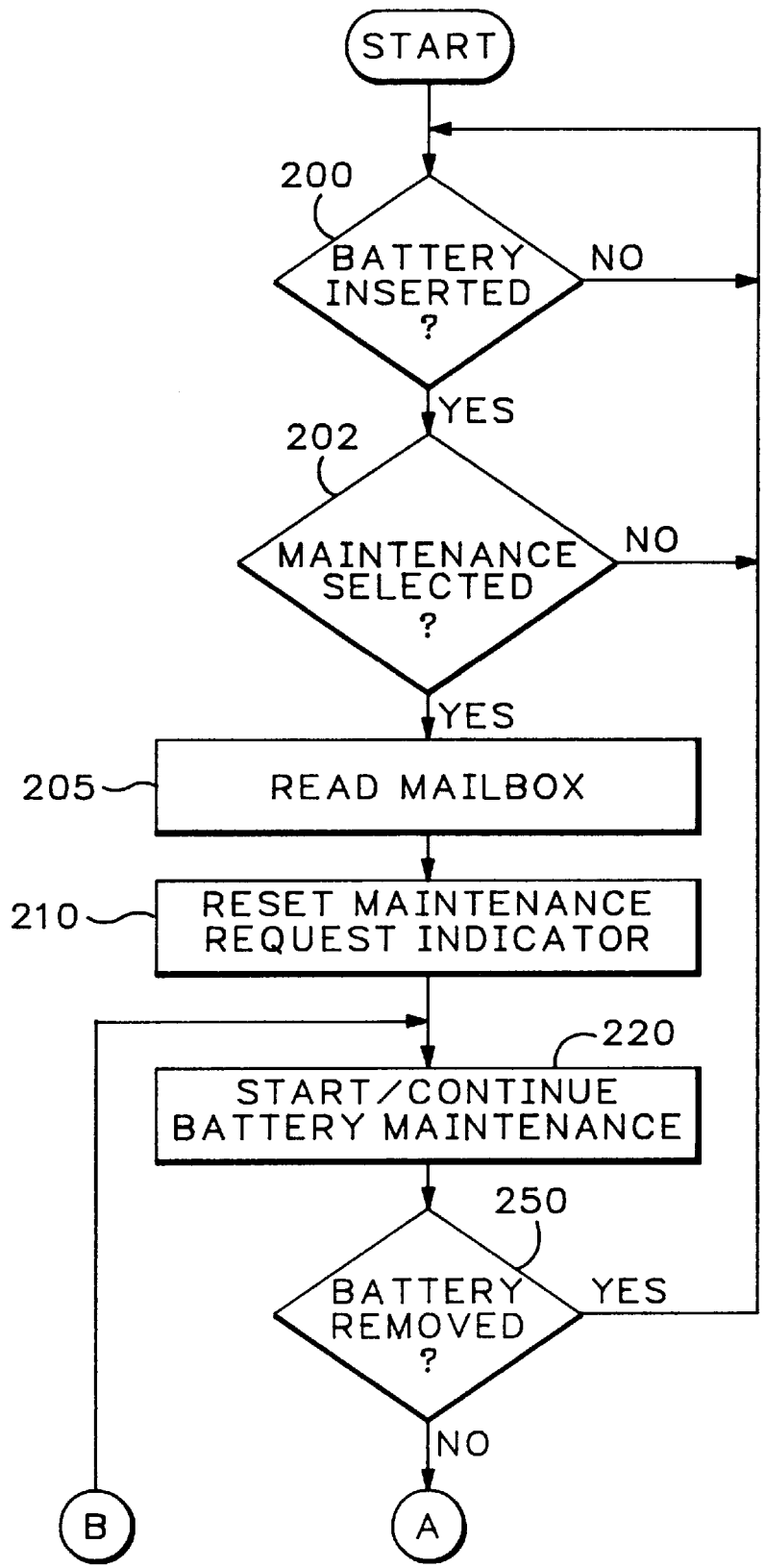
FIGS. 8–10 show the flowchart of the maintenance operation of the battery support unit of the preferred embodiment of the invention.
Figure 9:
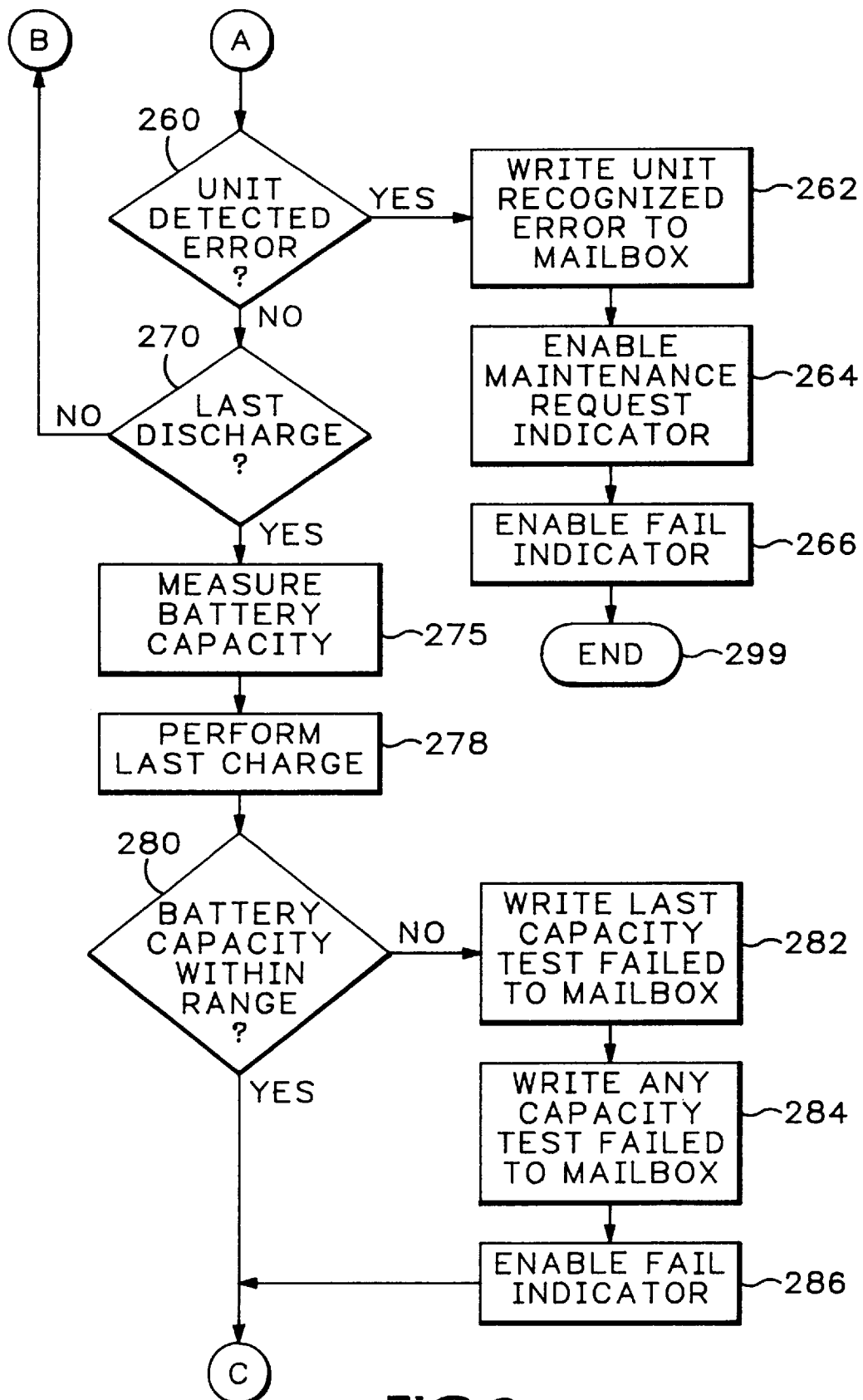
Figure 10:
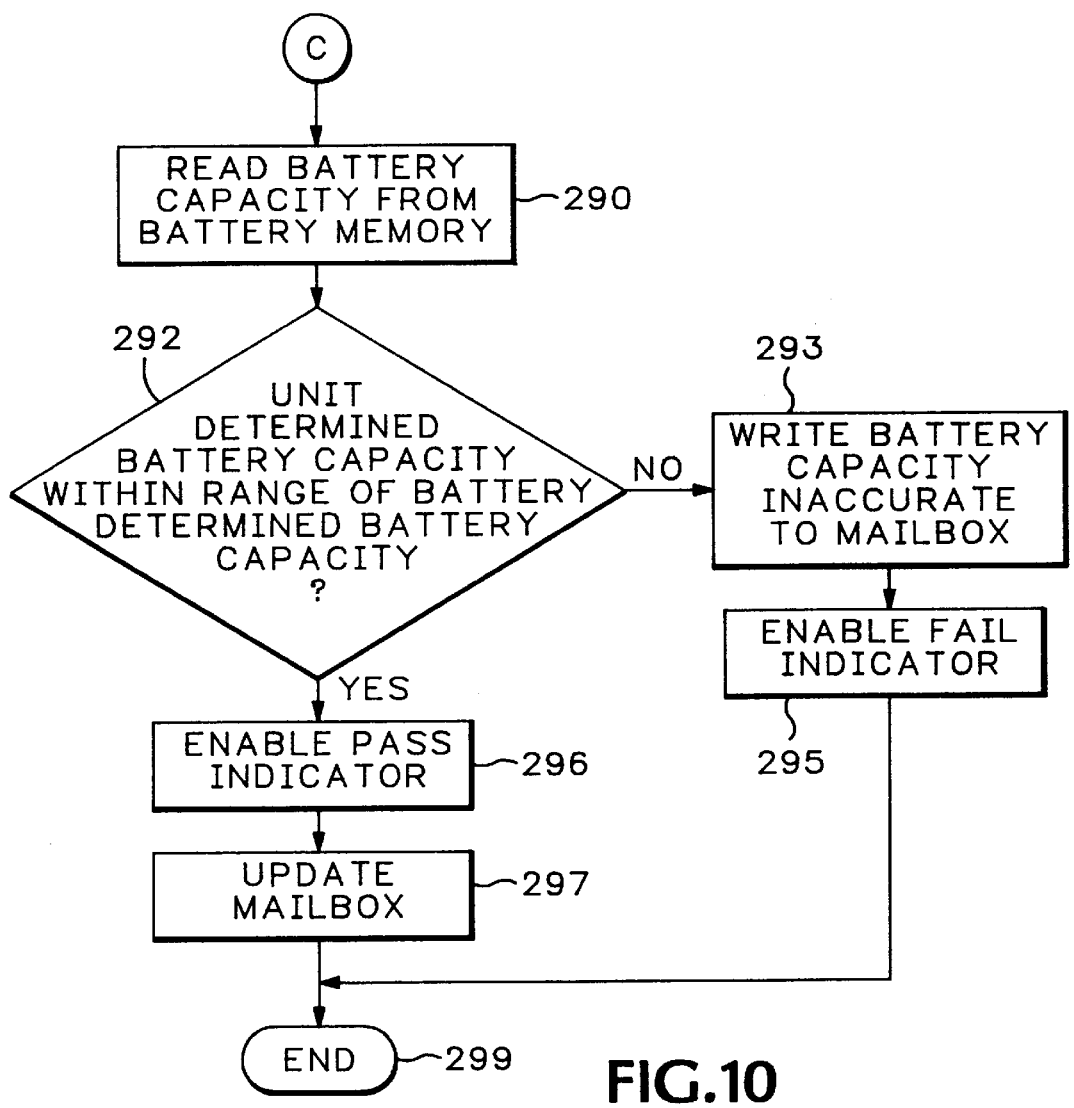

FIGS. 8–10 show the flowchart of the maintenance operation of battery support unit 20 of the preferred embodiment of the invention. Block 200 checks to see if a battery is inserted into the charger. When a battery is detected, block 202 checks to see if maintenance has been selected for this battery. In the preferred embodiment, maintenance is selected by the user pressing indicator button 62, although this selection operation could be performed in a different manner, such as automatically when an error is detected in block 160 of FIG. 7, as has been discussed, and still fall within the spirit and scope of the invention.

When block 202 is answered affirmatively, block 205 reads the contents of mailbox 50 by submitting a request to read data from the mailbox to battery 30. Block 210 resets maintenance request indicator 62.

Block 220 starts the maintenance operation. For purposes of this discussion, the term "maintenance" as used herein shall mean any operation performed on the battery, outside of a single charging operation, intended to prolong the useful life of the battery. For example, the useful life of a NiCad battery can be extended if it is "reconditioned" by charging and discharging the battery a predetermined number of cycles. In the preferred embodiment, maintenance of battery 30 involves the following steps:

1. Charge (trickle/full—typically 3 hours)
2. Cool (60 minutes)
3. Discharge (cleanse battery by fully discharging at a predetermined current drain)
4. Cool (60 minutes)
5. Charge (trickle/full—typically 3 hours)
6. Cool (5 minutes)
7. Supercharge (trickle—10 hours)
8. Cool (60 minutes)
9. Final Discharge (cleanse battery by fully discharging at a predetermined current drain)
10. Cool (60 minutes)
11. Final Charge (trickle/full—typically 3 hours)

Those skilled in the art will appreciate that other types of maintenance could be performed on the battery and still fall within the spirit and scope of the invention. For example, an alternate embodiment has been contemplated where only steps 9 and 11 above are performed during the maintenance operation.

During the maintenance operation, blocks 250–299 execute, looking for various conditions that can occur during the maintenance operation. Block 250 checks to see if the battery was removed before maintenance was complete. If so, flow of control returns back to block 200 to check for re-insertion of the battery. If not, block 260 checks for a support unit detected error that occurred during the maintenance operation. Examples of errors that can be detected by block 260 are the following: battery too hot, battery too cold, battery voltage too low, battery voltage too high, battery charging timeout (taking too long to charge). As previously discussed, battery support unit 20 determines if a temperature error has occurred by reading the voltage level on thermistor 35. Battery support unit 20 determines if a voltage error has occurred by using a portion of support unit circuitry 28 to measure the voltage across battery 30. Battery support unit 20 determines if a timeout error has occurred by using a timer in processor 21 or support unit circuitry 28 to keep track of the elapsed charging time.

If block 260 detects an error, block 262 writes a support unit recognized error to mailbox 50. This is done by placing a "1" in bit 1 of the word read from mailbox 50, adjusting checksum bits 6 and 7 accordingly, and sending the word back to battery 30 as a request to write data to mailbox 50. Block 264 turns on maintenance request indicator 62. Block 266 enables fail indicator 64 (FIG. 4), and the program ends in block 299.

If block 260 does not detect an error, block 270 checks to see if the maintenance operation has started the final discharge cycle. If not, flow of control returns to block 220 to continue the battery maintenance operation. If so, block 275 measures the capacity of the battery as the final discharge cycle is performed. This is done by keeping track of the amount of charge delivered from the battery during the final discharge cycle and comparing it with the theoretical capacity of the battery. Block 278 performs the last charge of battery 30. If the amount of charge delivered from the battery during the last discharge cycle is not within a predetermined range of the theoretical capacity of the battery, block 280 is answered negatively. Block 282 writes a last capacity test failed error to mailbox 50. This is done by placing a "1" in bit 4 of the word in mailbox 50. Block 284 writes an any capacity test failed error to mailbox 50. This is done by placing a "1" in bit 5 of mailbox 50, adjusting checksum bits 6 and 7 to account for the changes in the mailbox bits, and sending the word back to battery 30 as a request to write data to mailbox 50. Block 286 enables fail indicator 64 (FIG. 4), and flow of control moves to block 290 (FIG. 10). Flow of control also moves to block 290 if block 280 is answered affirmatively.

Referring now to FIG. 10, block 290 reads the battery capacity from battery memory 40. Specifically, block 290 sends a request to battery 30 to read the contents of NACH and NACL fields 41-4 and 41-5 in memory 40 (FIG. 2). Block 292 then checks to see if the support unit determined battery capacity (determined in block 275) is within range of the battery determined battery capacity (NACH and NACL registers). If not, the battery determined battery capacity is inaccurate, and block 293 writes a battery capacity inaccurate error to mailbox 50 by putting a "1" in bit position 2 and adjusting the checksum bits accordingly. Block 295 enables fail indicator 64. If block 292 is answered affirmatively, block 296 enables pass indicator 63 (FIG. 4). Block 297 writes updated mailbox data (zeroing out old errors, writing a "1" for new errors, and updating checksum bits) to mailbox 50. Regardless how block 292 is answered, flow of control eventually finds its way to block 299, where the program ends.

Figure 11:
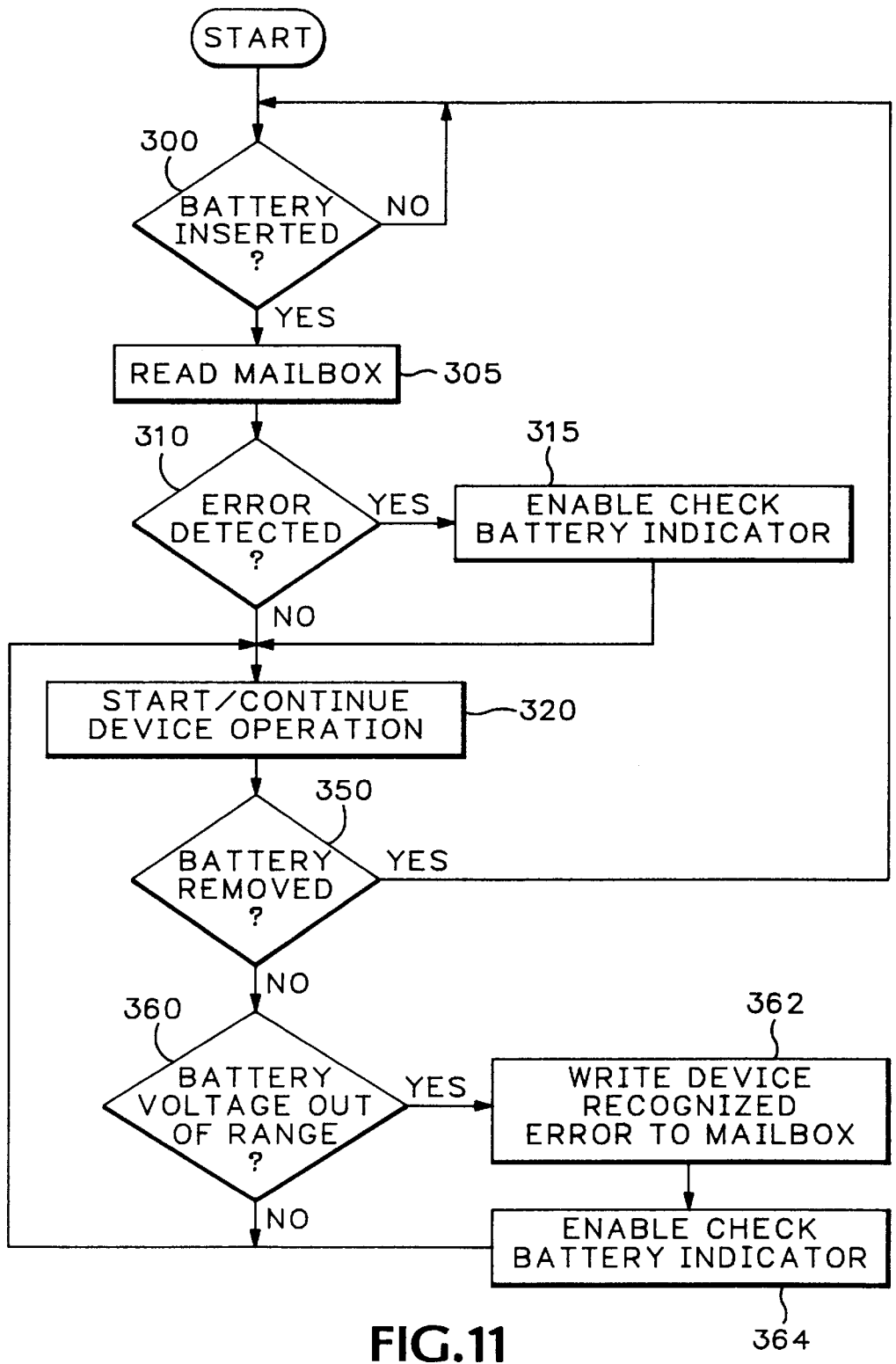
FIG. 11 shows the flowchart of the operation of the electronic device of the preferred embodiment of the invention.

FIG. 11 shows the flowchart of the operation of the electronic device of the preferred embodiment of the invention. Block 300 checks to see if a battery is inserted into the electronic device. When a battery is detected, block 305 reads the contents of mailbox 50 by submitting a request to read data from the mailbox to battery 30.

Block 310 checks to see if the data contained in mailbox 50 indicates that an error has occurred. Errors can be detected and indicated in mailbox 50 by one or more battery support units and/or one or more electronic devices. Block 310 checks to see if bits 0, 1, 2, or 4 is a "1". Note that a "1" in bit position 5, "Any Capacity Test Failed", is informational in nature and not considered an error of any by itself.

If block 310 determines that any of the above bits is a "1", block 315 enables indicator 91 in support unit user interface 90. In the preferred embodiment, this action displays indicator 91 as a "Check Battery" message on the display screen of electronic device 80, although other forms of indication could be used. In the preferred embodiment, maintenance is not performed by electronic device 80 but instead is performed by battery support unit 20.

Block 320 starts the device operation. This operation is highly dependent on the function of electronic device 80. For example, if electronic device 80 was a portable computer, block 320 would start normal computer operations. In the preferred embodiment, electronic device 80 is a defibrillator/heart monitor, so block 320 would initiate the normal operation of the defibrillator/heart monitor.

During the device operation, blocks 350–399 execute, looking for various conditions that can occur during the device operation. Block 350 checks to see if the battery was removed during the device operation. If so, flow of control returns back to block 300 to check for re-insertion of the battery. If not, block 360 checks to see if the battery voltage is out of range. Specifically, block 360 determines if the actual voltage decay over time as charge in the battery is depleted is within range of what is expected from the battery. Stated another way, block 360 periodically requests to read data from memory 40 of battery 30 (e.g., NACH/NACL registers 41-4 and 41-5) to make sure that the battery's information on how much charge it has left is based in reality, and that the voltage doesn't drop off too fast (i.e. voltage depression) and fail to give the user adequate warning of a low battery.

If block 360 detects an error, block 362 writes a device recognized error to mailbox 50. This is done by placing a "1" in bit 0 of the word read from mailbox 50, adjusting checksum bits 6 and 7 accordingly, and sending the word back to battery 30 as a request to write data to mailbox 50. Block 364 turns on check battery indicator 91, and flow of control returns to block 320 to continue device operation—at least until the battery dies. If block 360 determines the battery voltage is not out of range, flow of control also returns to block 320.

Figure 12:
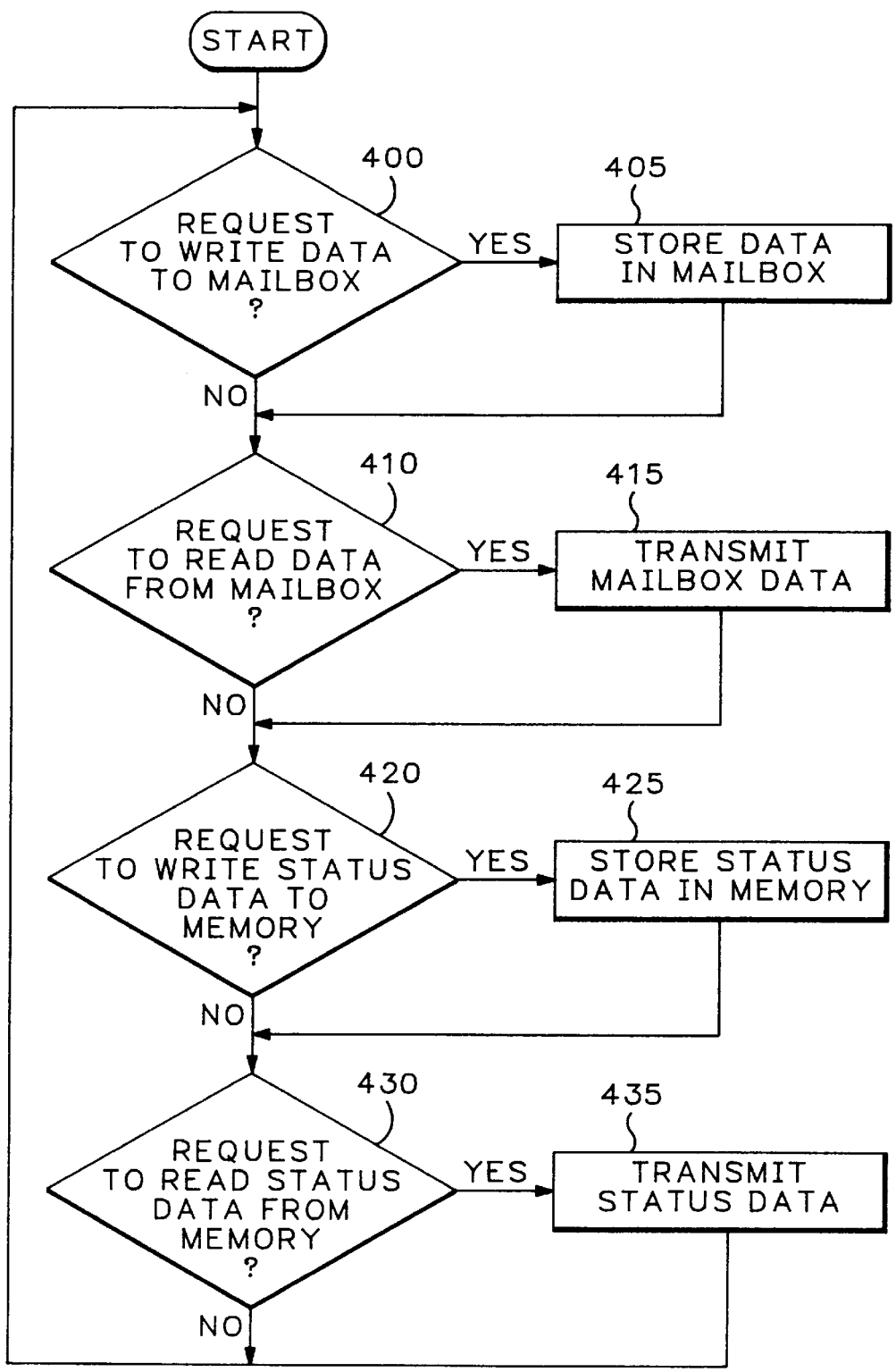
FIG. 12 shows the flowchart of the operation of the battery of the preferred embodiment of the invention.

FIG. 12 shows the flowchart of the operation of the battery of the preferred embodiment of the invention. The execution of the blocks shown in FIG. 12 do not require that an elaborate communications mechanism be present in battery 30—just the ability to have data read into and out of memory 40. As previously discussed, the batteries of various alternate embodiments (e.g., Econoram, EEPROM) contain a sufficient communications mechanism in memory 40 to perform the execution of the flowchart of FIG. 12. Block 400 checks to see if any requests have arrived from a battery support unit or an electronic device to write data to mailbox 50. In the preferred embodiment, these requests are submitted in two parts: Command+register address; data. If so, block 405 stores the data in mailbox 50. Block 410 checks to see if any requests have arrived from a battery support unit or an electronic device to read data from mailbox 50. If so, block 405 transmits the data contained in the specified register of mailbox 50 to the requester. Block 420 checks to see if any requests have arrived from a battery support unit or an electronic device to write status data to memory 40. While not discussed previously, some of the registers in memory 40 are writable fields, such as LMD field 41-6. If so, block 405 stores the data in the appropriate register of mailbox 50. Block 430 checks to see if any requests have arrived from a battery support unit or an electronic device to read status data from memory 40. If so, block 435 transmits the data contained in the specified register of memory 40 to the requester.

What is claimed is:

1. A method in a battery support unit for testing a battery having memory, said method comprising the steps of:

connecting said battery to said battery support unit;

testing said battery for a first error condition, wherein said first error condition indicates a first fault with the battery that may impact its future performance and not that the battery is discharged and needs to be recharged;

detecting said first error condition in said battery;

transmitting first error data to a mailbox located in said memory of said battery, responsive to detecting said first error condition; and disconnecting said battery from said battery support unit, said battery capable of connecting to an electronic device.

2. The method of claim 1, further comprising the steps of:

reading second error data in said mailbox, wherein said second error data was placed in said mailbox by an electronic device which used said battery, and wherein said second error data indicates a second fault with the battery that may impact its future performance and not that the battery is discharged and needs to be recharged; and enabling an indicator in response to said step of reading said second error data.

3. The method of claim 2, wherein said indicator instructs a user to perform maintenance on said battery.

4. The method of claim 1, further comprising the steps of:

reading second error data in said mailbox, wherein said second error data was placed in said mailbox by a second battery support unit which tested said battery, and wherein said second error data indicates a second fault with the battery that may impact its future performance and not that the battery is discharged and needs to be recharged;

enabling an indicator in response to said step of reading said second error data.

5. The method of claim 4, wherein said indicator instructs a user to perform maintenance on said battery.

6. The method of claim 1, further comprising the step of:

reading battery determined battery capacity data placed in said battery memory by said battery.

7. The method of claim 6, further comprising the steps of:

comparing said battery determined battery capacity data with support unit determined battery capacity data; and determining said battery determined battery capacity data is out of range with said support unit determined battery capacity data, thereby resulting in said first error condition.

8. The method of claim 1, further comprising the steps of:

detecting that maintenance for said battery has been selected; and discharging and charging said battery at least two times.

9. The method of claim 1, further comprising the step of:

sending validation data to said mailbox located in said memory of said battery, said validation data validating said first error data transmitted to said mailbox in said transmitting step.

10. A method in a battery support unit for testing a battery having memory, said method comprising the steps of:

connecting said battery to said battery support unit;

automatically performing maintenance on said battery by discharging and charging said battery at least two times; and disconnecting said battery from said battery support unit, said battery capable of connecting to an electronic device.

11. The method of claim 10, further comprising the step of:

reading error data from said memory of said battery, wherein said error data indicates that said battery needs maintenance and not that the battery is discharged and needs to be recharged.

12. A method in a first battery support unit for testing a battery having memory, said method comprising the steps of:

connecting said battery to said battery support unit;

reading error data in a mailbox located in said memory of said battery, wherein said error data was placed in said mailbox by a second battery support unit which used said battery and wherein said error data indicates a fault with the battery that may impact its future performance and not that the battery is discharged and needs to be recharged;

performing maintenance on said battery by discharging and charging said battery at least two times; and disconnecting said battery from said battery support unit, said battery capable of connecting to an electronic device.

13. A battery support unit for testing a battery having memory, said battery support unit comprising:

a processor further comprising battery test logic, wherein said battery test logic:

tests said battery for a first error condition, wherein said first error condition indicates a fault with the battery that may impact its future performance and not that the battery is discharged and needs to be recharged;

detects said first error condition in said battery; and transmits first error data to a mailbox located in said memory of said battery, responsive to detecting said first error condition.

14. The battery support unit of claim 13, wherein said battery test logic:

reads second error data in said mailbox, wherein said second error data was placed in said mailbox by an electronic device which used said battery, and wherein said second error data indicates a second fault with the battery that may impact its future performance and not that the battery is discharged and needs to be recharged; and enables an indicator in response to said reading said second error data.

15. The battery support unit of claim 13, wherein said battery test logic:

reads second error data in said mailbox, wherein said second error data was placed in said mailbox by a second battery support unit which tested said battery; and wherein said second error data indicates a second fault with the battery that may impact its future performance and not that the battery is discharged and needs to be recharged; and enables an indicator in response to said reading said second error data.

16. The battery support unit of claim 13, further comprising:

charger circuitry connected to said processor.

17. The battery support unit of claim 16, wherein said indicator instructs a user to perform maintenance on said battery.

18. The battery support unit of claim 16, wherein said first error condition is a battery too hot condition.

19. The battery support unit of claim 16, wherein said first error condition is a battery too cold condition.

20. The battery support unit of claim 16, wherein said first error condition is a battery voltage too high condition.

21. The battery support unit of claim 16, wherein said first error condition is a battery voltage too low condition.

22. The battery support unit of claim 16, wherein said first error condition is a battery charger timeout condition.

23. The battery support unit of claim 16, wherein said first error condition is a battery capacity out of range condition.

24. The battery support unit of claim 16, wherein said battery test logic reads battery determined battery capacity data placed in said battery memory by said battery.

25. The battery support unit of claim 24, wherein said battery test logic compares said battery determined battery capacity data with support unit determined battery capacity data.

26. The battery support unit of claim 25, wherein said first error condition is a battery capacity inaccurate condition, said first error condition resulting from the battery determined battery capacity data being out of range of the support unit determined battery capacity data.

27. The battery support unit of claim 25 wherein said processor further comprises battery maintenance logic, wherein said battery maintenance logic:

detects that maintenance for said battery has been selected;

charges and discharges said battery a predetermined number of times.

28. The battery support unit of claim 13, wherein said battery test logic:

sends validation data to said mailbox located in said memory of said battery, said validation data validating said first error data transmitted to said mailbox by said battery test logic.

29. A battery support unit for testing a battery having memory, said battery support unit comprising:

a processor further comprising battery test logic, wherein said battery test logic:

tests said battery for a first error condition;

detects said first error condition in said battery;

transmits first error data to a mailbox located in said memory of said battery, responsive to detecting said first error condition, said first error data readable by a first electronic device or a second battery support unit;

reads second error data in said mailbox, wherein said second error data was placed in said mailbox by said first electronic device or said second battery support unit; and enables an indicator in response to said reading said second error data.

30. The battery support unit of claim 29, wherein said battery test logic:

sends validation data to said mailbox located in said memory of said battery, said validation data validating said first error data transmitted to said mailbox by said battery test logic.

* * * * *